United States Patent [19]

Segura Badia

[11] Patent Number: 5,340,359
[45] Date of Patent: Aug. 23, 1994

[54] DISINFECTING CONNECTION FOR CATHETERS

[75] Inventor: Marcelo Segura Badia, Barcelona, Spain

[73] Assignee: L'Institut Municipal D'Assistencia Sanitaria, Barcelona, Spain

[21] Appl. No.: 33,464

[22] Filed: Mar. 18, 1993

Related U.S. Application Data

[63] Continuation of Ser. No. 827,324, Jan. 29, 1992, abandoned.

[30] Foreign Application Priority Data

Jan. 30, 1991 [ES] Spain ..................... 9100239

[51] Int. Cl.⁵ .......................................... A61M 25/00
[52] U.S. Cl. ..................... 604/283; 604/265; 604/411; 604/905
[58] Field of Search ............... 604/199, 201, 241, 243, 604/244, 265, 283, 411, 414, 905

[56] References Cited

U.S. PATENT DOCUMENTS 3,502,097  3/1970  Muller ..................... 604/86
4,354,490  10/1982  Rogers .
4,559,043  12/1985  Whitehouse et al. ............. 604/243
4,610,469  9/1986  Wolff-Mooijav ............. 604/411
4,919,658  4/1990  Segura Badia .
4,981,469  1/1991  Whitehouse et al. ............. 604/283

FOREIGN PATENT DOCUMENTS 0256640  2/1988  European Pat. Off. .
0298257  1/1989  European Pat. Off. ......... 604/905
2506162  11/1982  France ..................... 604/905
9007953  7/1990  PCT Int'l Appl. ........... 604/905

Primary Examiner—John D. Yasko
Assistant Examiner—Anthony Gutowski
Attorney, Agent, or Firm—Cushman, Darby & Cushman

[57] ABSTRACT

A disinfecting assembly for connecting needles and the like to catheters is characterized by a central body comprising two parts which may be engaged together to enclose an interchangeable disinfecting element. The central body at one of its ends receives a first terminal portion which is coupled to one piece of ducting carrying a needle. The needle punctures the disinfecting element incorporated within the central body. The central body receives at its other end a second terminal corresponding to a second piece of ducting to be associated with the connection.

11 Claims, 5 Drawing Sheets

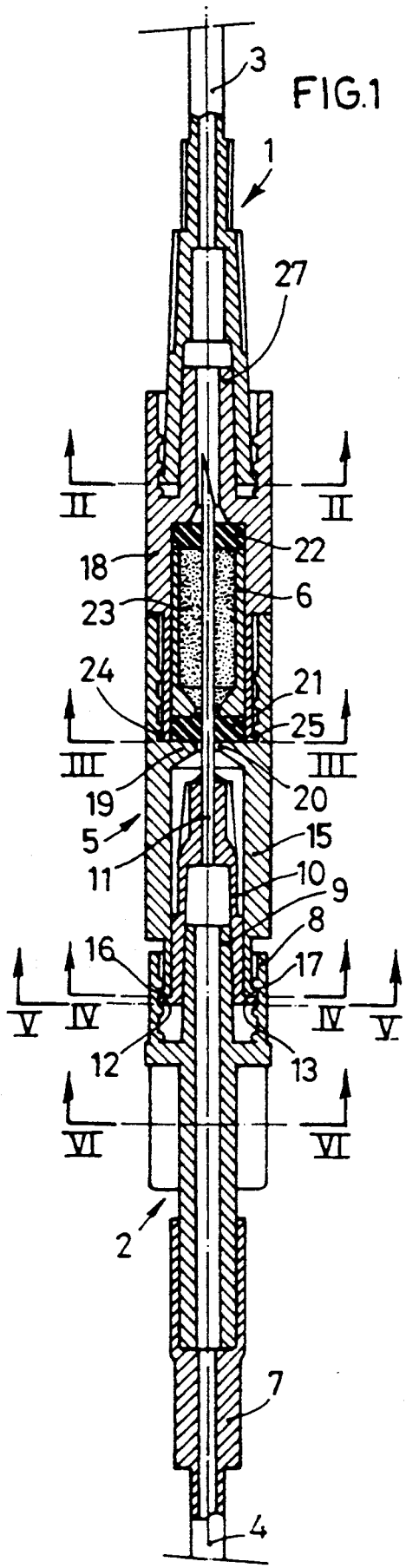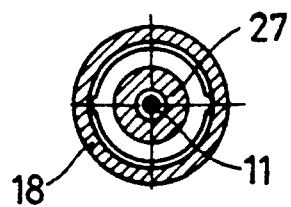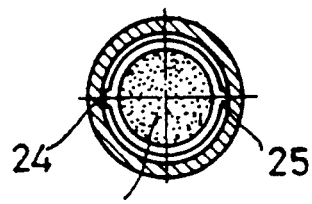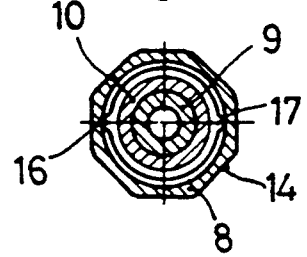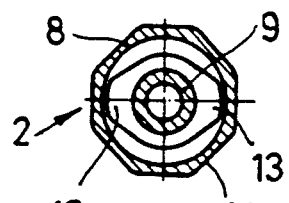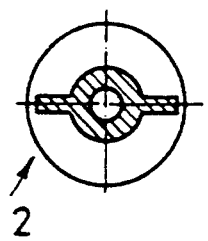

DISINFECTING CONNECTION FOR CATHETERS

This is a continuation of application Ser. No. 07/827,324, filed on Jan. 29, 1992, which is abandoned.

BACKGROUND OF THE INVENTION

This invention relates to a disinfecting connection for catheters and the like which has substantial advantages over what has been previously known in this field. The connection which is the subject of this invention will be applied to fluid conducting systems for catheters and other similar means by which the passage of fluid products to be incorporated to a human body is carried out. Various drug solutions and blood serum are examples of such fluid products.

In conducting systems for fluids to be incorporated to the human body, it is necessary to provide a means for the disinfection of the connection element, which usually consists of a needle.

European Patent Application 88108931.2 discloses a former embodiment of the same Applicant in which a solution is given to the problem of the complete and integral disinfection of the needle for the connection to the catheters. However, in this previous embodiment there was the problem of the eventual physical contact of the hand or other external bodies with the limiting end closure of the disinfecting element, where protection was not complete. Also, the center of the connecting needle with the disinfecting element was not completely safe because the needle was not properly guided during its insertion which could lead to a faulty location of the same, making a second insertion necessary.

Additionally, in the previously known embodiment, when the need arose to replace the disinfecting unit, the catheter which formed part of the same had to be replaced as well, which made necessary a new surgical procedure to insert a new catheter into the patient. That was particularly troublesome in cases of patients requiring a catheter for very long periods of time which in some cases could be years or may extend to the whole life of the patient.

SUMMARY OF THE INVENTION

This invention brings improvements on what presently known in this field, providing a complete connection for pipe conducting systems, which may be exchanged as a whole, having means for holding a disinfecting unit, which may be readily replaced and also the necessary means for the connection of the conducting systems to convey the solutions perfusion liquids to the human body.

Essentially, the connection of this invention consists of two parts, each to be attached respectively to one of the ends of two pieces ducting carrying the disinfecting means. The parts may be removably or fixedly attached to the duct which will allow therefore the possibility of being exchanged, without it being necessary to change the catheter. Such disinfecting means or disinfecting element, consists of a small internal cylinder having end closures preferably made of an elastic material which may be easily penetrated by a needle. The internal cylinder is filled with a disinfecting liquid. The needle will be incorporated in one of the ends of the above mentioned pieces of ducting, so that when it is coupled to the disinfecting element carrying the disinfecting means the needle will penetrate the elastic closures of the disinfecting means carrying body, reaching a position to allow the passage of the liquids to be perfused to the human body, maintaining the necessary sterilized conditions.

For the renewal of the disinfecting means when it is desired, it is sufficient to disconnect the central body carrying the disinfecting means, replacing the disinfecting element with a new one or replacing the whole central body. Alternatively, the renewal of the disinfecting element may be carried out together with the whole connection which is attached to the pieces of ducting.

An alternative embodiment of the present invention provides the coupling of the parts enclosing the disinfecting means by non-detachable welding, preventing possible serious accidents in case when during the dismantling of the piece of ducting carrying the needle, such dismantling might be accidentally carried out at the point of attachment of both parts enclosing the disinfecting unit whose contents could be spilled out or could lead to the entrance of air into the catheter due to the dislodging.

Therefore, the present invention is characterized by a central body comprising two parts which may be engaged together, which carry an interchangeable disinfecting element. A terminal portion which is coupled to one of the pieces of ducting to be attached to the connection and carrying the needle aimed at traversing the disinfecting element is attached to one end of the central body. The central body receives in its other end a second terminal corresponding to the second piece of ducting to be associated with the connection.

Another feature of this invention is that the terminal carrying the needle is pressure fitted on one end into an expanded end of the corresponding piece of ducting, while at the other end it has a cuplike part with internal threading aimed at receiving the corresponding part of the central body which carries the disinfecting element. The other end has as well an axial expansion aimed at allowing the pressure engagement of the base of the needle.

Additionally, this invention is characterized in that the central body which carries the disinfecting element is composed of two parts which may be readily engaged together. One of the parts mates with the internal threading of the corresponding terminal by means of protrusions in its lower border, while the other receives in its cuplike end the protrusions constituted on the end of the corresponding terminal of the other piece of ducting.

Further, this invention is characterized in that the part of the central body receiving the needle has an intermediate partition with a hole for the passage of said needle, and to receive one of the end faces of the disinfecting element which is constituted by a cylindrical body located within a housing of similar form of the other part which constitutes the central body of the connection and having end closures made up of an elastic material which may be penetrated by the needle and which close the chamber carrying the disinfecting liquid.

Finally, this invention is also characterized in that the two parts constituting the body which contain the disinfecting unit may be permanently assembled together by means of welding at the abutment areas of upper and lower parts on a protruding ring of the body containing the disinfecting product.

For its better understanding, some explanatory drawings are enclosed, which should be understood as nonlimiting examples of disinfecting connections which incorporate the principles of this invention.

BRIEF DESCRIPTION OF THE DRAWINGS

FIG. 1 is a longitudinal section of a connection according to the present invention.

FIGS. 2, 3, 4, 5 and 6 are cross-sections by the planes indicated in FIG. 1.

DESCRIPTION OF THE PREFERRED EMBODIMENTS

Figure 7:
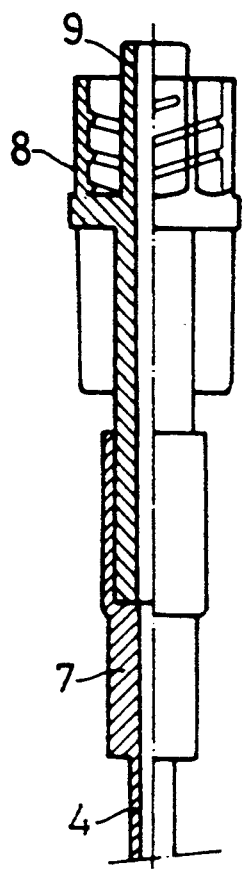
FIG. 7 is a section of the connection part receiving the needle.
Figure 9:
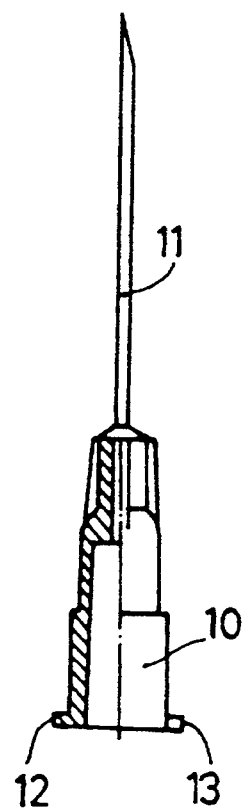
FIGS. 9 and 10 correspond respectively to a longitudinal section and to an upper view of the cap carrying the connection needle.
Figure 8:
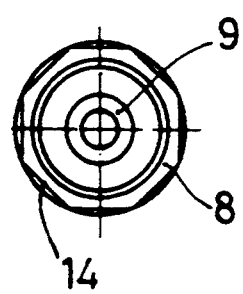
FIG. 8 is an upper view corresponding to FIG. 7.
Figure 10:
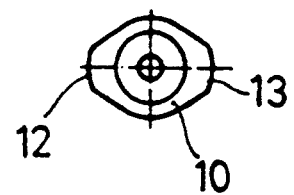
Figure 11:
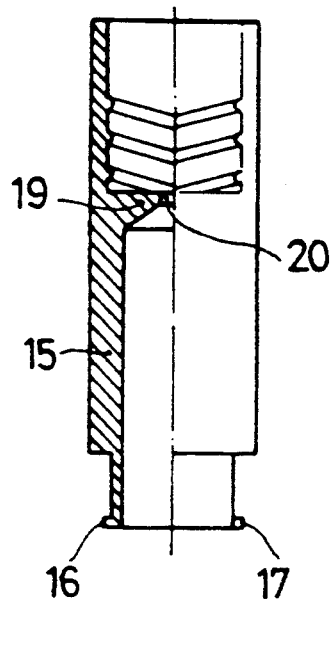
FIGS. 11 and 12 correspond to a longitudinal section and to an upper view, respectively, of one of the parts forming the body which carries the disinfecting element.
Figure 13:
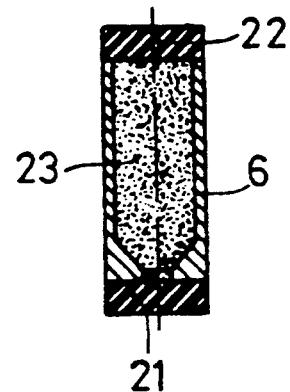
FIG. 13 corresponds to a longitudinal section of the disinfecting element.
Figure 12:
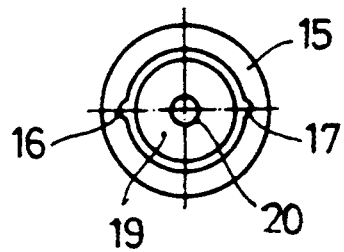
Figure 14:
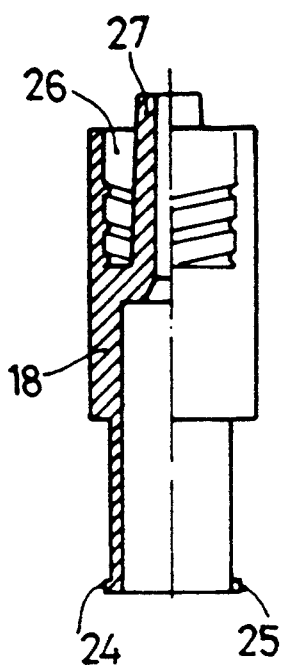
FIGS. 14 and 15 show respectively a longitudinal section and an upper view of the second part forming the body carrying the disinfecting element.
Figure 16:
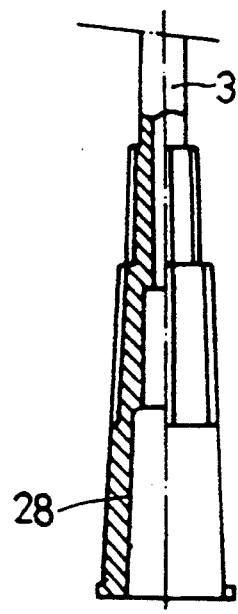
FIGS. 16 and 17 correspond respectively to a longitudinal section and to an upper view of the terminal portion of one of the pieces of ducting.
Figure 15:
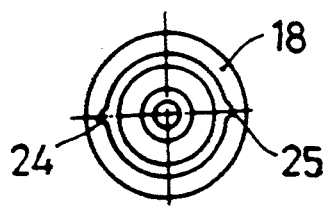
Figure 17:
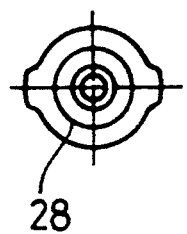
Figure 18:
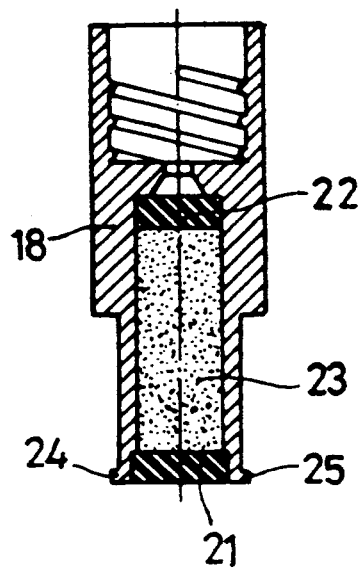
FIGS. 18 and 19 correspond respectively to a longitudinal section and to an upper view of the body of the connection carrying the disinfecting unit.

According to FIG. 1, the disinfecting connection of this invention consists of two terminals, 1 and 2, forming part of or to be attached at one end to the pieces of ducting 3 and 4 and to be connected at the other end to the body 5 carrying the exchangeable disinfecting element 6.

The arrangement is such as to allow the ready assembly and disassembly of the connection, obtaining at the same time the disinfecting effect on the needle and also the easy replacement of the disinfecting unit which are the objectives of the invention.

To that end, terminal 2 is attached by one of its ends to an expansion 7 of ducting 4 and at the other end, it has a cuplike part 8 having internal attachment grooves and having an internal tubular expansion 9 for receiving the base 10 of needle 11. The needle base will be pressure fitted, abutting on the end, to the outside of said tubular expansion 9 of the terminal 2.

In this way, the piece of ducting 4 and the terminal 2 together with the needle, constitute one of the parts to be attached to the central body 5. Whenever a new perfusion cycle has to be started, the terminal 2 may be quickly disassembled and assembled anew on body 5.

For the quick coupling of needle base 10 on grooves of the cuplike part 8, said needle base 10 has two opposed diametral protrusions 12 and 13 which mate with such grooves as may be seen in FIGS. 1 and 5.

The cuplike part 8 has on its outside surface flat faces 14 to ease its attachment and detachment by hand.

The body 5 which houses the disinfecting element 6 is constituted by parts 15 and 18 which, in this embodiment, may be pressure fitted or engaged by means of screw threads.

The part 15 has an internal partition 19 with a hole 20 to allow the guidance and passage of the needle. In its lower part, it has two protrusions 16 and 17, for engaging the internal threading of terminal 2.

The disinfecting element 6, which is interchangeable, contains the disinfecting liquid 23 and has elastic closures 21 and 22 on its ends, which will be penetrated by the needle 11.

Referring to FIGS. 14–19, part 18 of the central body has in its lower rim, two protrusions 24 and 25, and in the other end, it has a housing 26 with internal threading. A central expansion 27 protrudes upwards from part 18, for receiving the terminal 1, which has an internally tapered housing 28 mating with the external conical form of the expansion 27.

Figure 20:
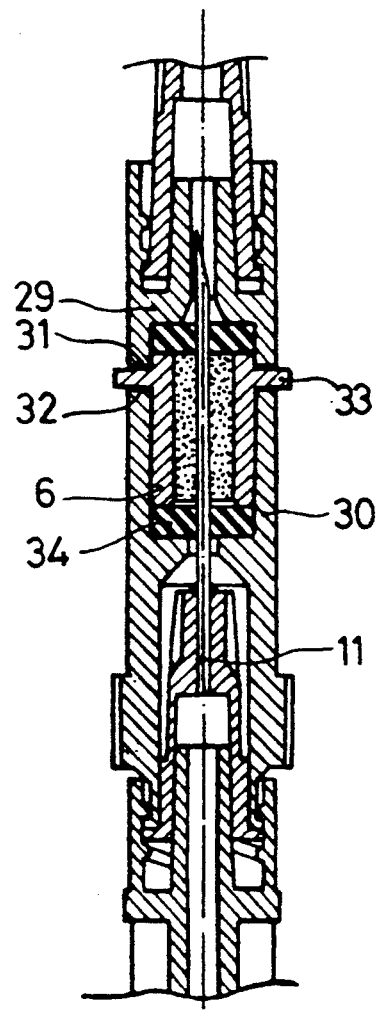
FIG. 20 is a longitudinal section of an alternate embodiment.
Figure 19:
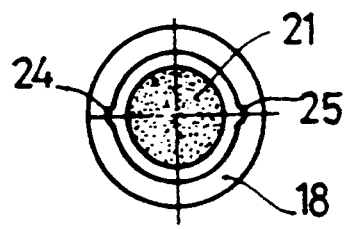

Another embodiment illustrated in FIG. 20 shows the arrangement of the disinfecting element 6 between an upper part and a lower part respectively 29 and 30 of the connection. The attachment of such parts will be fixed, by means of welding or similar means, at the abutment of faces 31 corresponding to upper part 29 and 32 corresponding to lower part 30. The body 6 carrying the disinfecting product has a protruding ring 33 which has a diameter which slightly exceeds the external diameter of upper and lower parts 29 and 30, providing the abutment faces. The attachment of both parts 29 and 30 could also be carried out directly.

It is possible in this way to establish efficient protection against physical contact on the end closure 34 of the disinfecting unit. At the same time, the accidental disassembly of the end closure for the disinfecting unit will be prevented.

By the above described means, it will be possible to carry out the quick engagement and disengagement of the two pieces of ducting enabling the disinfecting unit to be easily and aseptically interchanged.

As will be understood, many modifications could be carried out in the above-described embodiment of this invention, without departing from the scope of the following claims.

What is claimed is:

1. A disinfecting connection for catheters and the like comprising:
    a central body, the central body comprising:
    a first central part having a longitudinal axis, a first terminal engaging portion at one end thereof, and a tubular portion at another end thereof;
    a second central part having a longitudinal axis, a second terminal engaging portion at one end thereof, and a tubular portion at another end thereof, the tubular portion of the second central part being connected to the tubular portion of the first central part, the tubular portions together defining a disinfecting element receptacle; and
    a disinfecting element disposed within the disinfecting element receptacle, said disinfecting element comprising a central disinfecting portion containing a disinfecting material and two penetrable end closures, said tubular portion of said first central part and said tubular portion of said second central part each having an internal diameter at least as great as an outer diameter of said disinfecting element;
    a first terminal part having a longitudinal axis and a hollow needle attached to a first end thereof, the first terminal part being coupled at a second end thereof to a fluid conduit, the first end of the first terminal part being coupled to the first engaging portion of the firs central part such that the needle extends through the first central part along the longitudinal axis thereof, through a first of the penetrable end closures of the disinfecting element, traverses the central disinfecting portion and through a second of the penetrable end closures; and a second terminal part having a longitudinal axis and coupled at one end thereof to a fluid conduit, and coupled at a second end thereof to the second terminal engaging portion of the second central part, such that needle of the first terminal part is removably inserted through the disinfecting element and becomes disinfected when the first terminal part is connected to the central body to form a fluid passage therethrough.

2. A disinfecting connection for catheters and the like according to claim 1, wherein one of the tubular portions of the first and second central parts telescopingly receives the other of said tubular portions to allow for replacement of the disinfecting element.

3. A disinfecting connection for catheters and the like according to claim 2, wherein the first terminal part further comprises:

a cuplike portion located on the first end of the terminal part, the cuplike portion having internal threads for receiving the first terminal engaging portion of the central body;

an axial expansion portion at a base of the needle on the first end of the first terminal part; and a friction fit portion on the second end of the first terminal part which is removably pressure fitted to an expansion portion on an end of the fluid supply means.

4. A disinfecting connection for catheters and the like according to claim 2, wherein:

the first central part further comprises protrusions disposed upon the first terminal engaging portion for engaging the first terminal part; and the second terminal receiving portion of the second central part further comprises a cuplike portion having inner threads for receiving the second terminal part, the second terminal part having protrusions which interconnect with the inner threads of the cuplike portion of the second central part.

5. A disinfecting connection for catheters and the like according to claim 4, wherein the first central part has a partition having an aperture defined therein such that when the first terminal part is engaged with the first central part on one side of the partition, the needle passes through the aperture in the partition, and the disinfecting element is adjacent another side of the partition.

6. A disinfecting connection for catheters and the like according to claim 2, wherein the needle has a sharp, piercing tip and wherein the end closures of the disinfecting element are at opposite ends of the central disinfecting portion, the end closures being of a material which may be penetrated by the needle.

7. A disinfecting connection for catheters and the like according to claim 1, wherein the first and second central parts are permanently connected together by welding the tubular portions of the first and second central parts to a protruding ring portion of the disinfecting element.

8. A disinfecting connection for catheters and the like according to claim 7, wherein the first terminal part further comprises:

a cuplike portion located on the first end of the terminal part, the cuplike portion having internal threads for receiving the first terminal engaging portion of the central body;

an axial expansion portion at a base of the needle on the first end of the first terminal part; and a friction fit portion on the second end of the first terminal part which is removably pressure fitted to an expansion portion on an end of the fluid supply means.

9. A disinfecting connection for catheters and the like according to claim 7, wherein:

the first terminal engaging portion of the first central part further comprises protrusions to engage the first terminal part;

the second terminal receiving portion of the second central part further comprises a cuplike portion with inner threads for receiving the second terminal; and the second terminal part further comprises protrusions on the second end which interconnect with the inner threads of the cuplike portion.

10. A disinfecting connection for catheters and the like according to claim 9, wherein the first central part has a partition having an aperture defined therein such that when the first terminal part is engaged with the first central part on one side of the partition, the needle passes through the aperture in the partition, and the disinfecting element is adjacent another side of the partition.

11. A disinfecting connection for catheters and the like according to claim 7, wherein the needle has a sharp, piercing tip and wherein the end closures of the disinfecting element are at opposite ends of the central disinfecting portion, the end closures being of a material which may be penetrated by the needle.

* * * * *

UNITED STATES PATENT AND TRADEMARK OFFICE
CERTIFICATE OF CORRECTION

PATENT NO. : 5,340,359
DATED : August 23, 1994
INVENTOR(S) : SEGURA BADIA

It is certified that error appears in the above-identified patent and that said Letters Patent is hereby corrected as shown below:

On the Title page:

Item [73] should read

Assignee: L'Institut Municipal D'Assistencia
                 Sanitaria, Barcelona, Spain
                 1/2 undivided interest Signed and Sealed this Sixteenth Day of April, 1996

Attest:

BRUCE LEHMAN

Attesting Officer      Commissioner of Patents and Trademarks